(12) United States Patent
Teschner et al.

(10) Patent No.: US 8,321,007 B2
(45) Date of Patent: Nov. 27, 2012

(54) APPARATUS AND METHOD TO DETERMINE FUNCTIONAL LUNG CHARACTERISTICS

(75) Inventors: Eckhard Teschner, Lübeck (DE); Ola Stenqvist, Viken (SE)

(73) Assignee: Dräger Medical GmbH, Lübeck (DE)

( * ) Notice: Subject to any disclaimer, the term of this patent is extended or adjusted under 35 U.S.C. 154(b) by 280 days.

(21) Appl. No.: 12/702,590

(22) Filed: Feb. 9, 2010

(65) Prior Publication Data

US 2010/0228143 A1     Sep. 9, 2010

(30) Foreign Application Priority Data

Mar. 9, 2009  (EP) .................................. 09003376.2

(51) Int. Cl.
*A61B 5/053*     (2006.01)
*A61B 5/08*      (2006.01)
*A61B 5/085*     (2006.01)
*A61B 5/087*     (2006.01)

(52) U.S. Cl. ........ 600/547; 600/529; 600/533; 600/534; 600/536; 600/538; 128/204.23

(58) Field of Classification Search ............ 128/204.23; 600/529, 533, 534, 536, 538, 547
See application file for complete search history.

(56) References Cited

U.S. PATENT DOCUMENTS

| | | | |
|---|---|---|---|
| 5,660,170 A * | 8/1997 | Rajan et al. ............... | 128/204.18 |
| 6,551,252 B2 * | 4/2003 | Sackner et al. ................ | 600/536 |
| 7,096,061 B2 * | 8/2006 | Arad ............................. | 600/547 |
| 7,122,010 B2 | 10/2006 | Boehm et al. | |
| 7,435,226 B2 | 10/2008 | Suarez | |
| 7,787,946 B2 * | 8/2010 | Stahmann et al. ................ | 607/3 |
| 7,941,210 B2 * | 5/2011 | Matthiessen et al. ......... | 600/547 |

(Continued)

FOREIGN PATENT DOCUMENTS

DE     102006018198     10/2007

(Continued)

OTHER PUBLICATIONS

Torsten Meier et al.; Assessment of regional lung recruitment and derecruitment during a PEEP trial based on electrical impedance tomography; Intensive Care Med (2008) 34:543-550; Published online Jul. 25, 2007; copyright Springer-Verlag 2007.

(Continued)

*Primary Examiner* — Sean Dougherty
(74) *Attorney, Agent, or Firm* — McGlew and Tuttle, P.C.

(57) ABSTRACT

An apparatus for determining functional lung characteristics of a patient includes an electrical impedance tomography (EIT) imaging device adapted to record the impedance distribution within a plane of the thorax of the patient. The EIT imaging device includes a control and analysis unit for performing the impedance measurement and deriving the impedance distribution within the plane of the thorax. The control and analysis unit automatically performs steps including determining a global impedance change, defined as the impedance change with respect to an earlier measured reference impedance distribution integrated over the electrode plane, and recording the global impedance change curve as a function of time, performing breath detection in order to identify a breathing cycle, subdividing each breathing cycle to define a plurality of intratidal intervals, subdividing an EIT image from each interval into a plurality of regions of interest and calculating for each region of interest the ratio of the integrated impedance change within this region of interest to the global impedance change of this EIT image, for each intratidal interval presenting indications of the ratios determined for the regions of interest to provide an intratidal gas distribution representation for each interval.

20 Claims, 8 Drawing Sheets

Total volume:      100 %

ROI 1: Ventral:      29 %

ROI 2: Mid ventral:  52 %

ROI 3: Mid dorsal:   17 %

ROI 4: Dorsal:        2 %

U.S. PATENT DOCUMENTS

| | | | |
|---|---|---|---|
| 2002/0193700 A1* | 12/2002 | Bohm et al. | 600/533 |
| 2003/0095692 A1* | 5/2003 | Mundy et al. | 382/128 |
| 2003/0135127 A1* | 7/2003 | Sackner et al. | 600/536 |
| 2003/0216664 A1* | 11/2003 | Suarez | 600/547 |
| 2004/0073130 A1* | 4/2004 | Bohm et al. | 600/547 |
| 2004/0133123 A1 | 7/2004 | Leonhardt et al. | |
| 2005/0107719 A1* | 5/2005 | Arad | 600/547 |
| 2006/0178579 A1* | 8/2006 | Haynes | 600/437 |
| 2006/0260611 A1 | 11/2006 | Garber et al. | |
| 2007/0246047 A1 | 10/2007 | Teschner et al. | |
| 2007/0276270 A1* | 11/2007 | Tran | 600/508 |
| 2009/0069708 A1* | 3/2009 | Hatlestad et al. | 600/547 |
| 2009/0203972 A1* | 8/2009 | Heneghan et al. | 600/301 |

FOREIGN PATENT DOCUMENTS

| | | |
|---|---|---|
| DE | 102006018199 | 10/2007 |
| EP | 1 000 580 | 5/2000 |
| EP | 1 137 365 | 10/2001 |
| EP | 1 292 224 | 3/2003 |
| EP | 1 593 341 A | 11/2005 |
| WO | WO 91/19454 | 12/1991 |

OTHER PUBLICATIONS

Roy G. Brower, M.D., et al.; Ventilation With Lower Tidal Volumes As Compared With Traditional Tidal Volumes For Acute Lung Injury and the Acute Respiratory Distress Syndrome; The New England Journal of Medicine; Copyright 2000 by the Massachusetts Medical Society; vol. 342, No. 18, pp. 1301-1308; May 4, 2000.

Peter M. Suter, M.D. et al.; Optimum End-Expiratory Airway Pressure in Patients With Acute Pulmonary Failure; The New England Journal of Medicine; Feb. 6, 1975; pp. 284-289.

Keith G. Hickling, M.D.; Reinterpreting the pressure-vol. curve in patients with acute respiratory distress syndrome; Curr Opin, Crit Care Med 2007; 35:214; "Not Published"; 7 pages.

Fernando Suarez-Sipmann, M.D. et al.; Use of dynamic compliance for open lung positive end-expiratory pressure titration in an experimental study; Copyright Lippincott Williams & Wilkins; Crit Care Med 2007 vol. 35, No. 1; pp. 214-221.

* cited by examiner

| | | |
|---|---|---|
| Total volume: | | 100 % |
| ROI 1: | Ventral: | 29 % |
| ROI 2: | Mid ventral: | 52 % |
| ROI 3: | Mid dorsal: | 17 % |
| ROI 4: | Dorsal: | 2 % |

APPARATUS AND METHOD TO DETERMINE FUNCTIONAL LUNG CHARACTERISTICS

CROSS REFERENCE TO RELATED APPLICATIONS

This application claims the benefit of priority under 35 U.S.C. §119 of European Patent Application EP 09 003 376.2 filed Mar. 9, 2009, the entire contents of which are incorporated herein by reference.

FIELD OF THE INVENTION

The present invention relates to an apparatus and a method for determining functional lung characteristics of a patient utilizing an electrical impedance tomography (EIT) imaging device adapted to record the impedance distribution within a plane of the thorax of the patient, the EIT imaging device including a control and analysis unit for performing the impedance measurement and deriving the impedance distribution within the plane of the thorax (EIT image).

BACKGROUND OF THE INVENTION

Electrical impedance tomography (EIT) is an imaging technique in which an image of the impedance distribution of a part of the body is inferred from surface electrical measurements. EIT is a non-invasive method in which an alternating current of a few mA with a frequency of for example 50 kHz is fed into the human body and the resulting surface potentials are measured at different points around the body, using either conventional ECG electrodes or customized electrode belts. Two-dimensional distribution images or tomograms can be generated, which represent the distribution of the bioelectrical properties in one cross-sectional plane defined by the position of the electrodes around the thorax, by the successive rotation of the current feed points and the simultaneous measurements of the resulting surface potentials and by applying mathematical reconstruction algorithms to obtain the images. Such tomograms of the distribution of bioelectrical properties are of special interest in medicine in particular for determining functional lung characteristics, because the electrical impedance of lung tissue changes with the air content. It has been shown that ventilation induced impedance changes and volume changes show a high correlation with data determined with computer tomography (T. Meier at al., Intensive Care Med. (2008) 34: 543-550).

The basic principle for recording impedance distribution data using an electrical impedance tomography system is for example described in WO 91/19454 in which also the basic principles of the projection algorithms for deriving the image data are described.

There have also already been approaches how EIT could be used to monitor the effects of ventilation therapy and to control the ventilation therapy, as for example in DE 10 2006 018 198 A1 and DE 10 2006 018 199 A1. In these publications the underlying general approach is to always compare two different states with each other and to control a connected ventilator (also known as a respirator) based on the determined differences.

In EP 1 137 365 A1 the general approach described is to use a ventilator to apply two different pressures and to use EIT to analyze the impedance changes induced by this pressure change to determine the opening pressure of lung zones.

In EP 1 292 224 A1 a method for displaying information obtained by electrical impedance tomography data is described. In particular it is described that various screen modes of an EIT monitor are automatically adjusted based on pathological conditions. In this respect a phase lag mode is specifically described which analyzes the time delay (phase lag) of regional end-inspiratory or end-expiratory peaks. While the phase lag mode analyzes the delay of the regional beginning of inspiration in a complete breath it is not sensitive to changes occurring within the inspiratory and expiratory phase, therefore does not allow a detailed analysis of functional lung characteristics.

Another known measuring system for electrical impedance tomography is described in EP 1 000 580 A1 in which the graphic display of the measured impedance values is superimposed by the display for the same body slice in order to allow a more accurate evaluation of the measurements performed by means of electrical impedance tomography.

Functional lung characteristics which have been identified as particularly useful in connection with the present invention are the contributions of particular areas of the lung to the total tidal breathing activity at various times over the breathing cycle, or in other words the intratidal gas distribution over the lung. The determination of such functional lung characteristics would be useful to provide adapted settings for the individual patient of artificial respiration equipment. It has been found that from such characteristics setting parameters for artificial respiratory systems may be derived, such as the positive end-expiratory pressure (PEEP), the tidal volume (VT), the expiration time ($T_e$) and the susceptibility of the lung to a so-called recruitment maneuver.

Selecting optimal PEEP and appropriate tidal volume is a difficult task. Widely accepted practice is to use a tidal volume of 6 ml/kg predicted body weight (ARDSnet N. Engl J Med 2000; 342:1301) in spite of the fact that such a tidal volume may well be too large for a "baby lung" of an ALI/ARDS patient, but is at least better than the tidal volumes of 9-12 ml/kg that have been used previously. Selection of optimal PEEP is a real challenge with no satisfying practical answer today.

Originally PEEP was set to optimize oxygenation or oxygen delivery (Suter et al. N Engl J Med 1975; 292:284) but today PEEP is set to mechanically stabilize the lung, i.e. to avoid cyclic opening and collapse. The golden standard, performing a static PV curve and setting PEEP above the lower inflection point and plateau pressure below the upper inflection point at the straight part of the PV curve is not done at the bedside, except in research environments. It is also important to realize that during the straight part of the PV curve recruitment and overstretching of lung regions may occur simultaneously (Hickling. Curr opin, Crit Care 2002; 8:32). Therefore, with the use of these settings, there is no guarantee that cyclic opening and closing are not accompanied by overstretching as well.

A complicated way to set PEEP has been suggested by using CT images, but obviously this is a very "unclinical" method that cannot be used routinely. In the absence of practical clinical methods PEEP is normally set by a combination of an approximation of lung mechanics and oxygenation criteria. Recently, it has been shown that PEEP could be set by monitoring dynamic compliance (tidal volume/end-inspiratory pause pressure-end-expiratory pressure) (Suarez-Sipmann et al. Crit Care Med 2007; 35:214), but this has so far only been done in a surfactant deficient pig model, and furthermore dynamic compliance is a fairly insensitive indicator to properly set PEEP in ALI/ARDS patients. This method relies on opening the lung completely before the PEEP step down procedure. The peak pressure (60 cmH$_2$O) applied to the lung is quite high and could be dangerous as it involves the risk of developing pneumothorax in patients.

Another method for optimization of PEEP and tidal volume is described in EP 1 108 391 A1 which proposes to determine a so-called pulmonary stress index from the pressure time relationship. However, as recruitment and overstretching may occur simultaneously, these conditions might remain undetected due to the fact that these concurrent effects are masked in the global pressure curve, which only reflects the overall behavior and resulting effects of the inhomogeneous lung as a whole.

SUMMARY OF THE INVENTION

It is the object of this invention to provide an apparatus and a method to determine functional lung characteristics, which are indicative of the breathing activity of lung areas, which may be used to define such things as PEEP and tidal volume as well as appropriateness and susceptibility to recruitment maneuvers (RM). In particular, it would be preferred if the apparatus and the method would be applicable in a non-invasive manner and would be usable continuously at the bedside. In particular, the apparatus and the method should allow determining the PEEP level and tidal volume that is required to open up collapsed lung regions and to keep the balance between the goals to avoid atelectotrauma and overdistension. Furthermore, it would be preferred if the apparatus and the method are able to provide an indication in which patients a recruitment maneuver (RM) will be beneficial to differentiate responders from nonresponders to RM. Finally, the apparatus and the methods should allow displaying functional lung parameters in value which is easily perceived and interpreted.

These and other objects are obtained by an apparatus for determining functional lung characteristics of a patient comprising an electrical impedance tomography (EIT) imaging device adapted to record the impedance distribution within a plane of the thorax of the patient, the EIT imaging device including a control and analysis unit for performing the impedance measurement and deriving the impedance distribution within the plane of the thorax (EIT image), characterized in that the control and analysis unit is further arranged to automatically perform the following steps:
  determining the global impedance change, defined as the impedance change with respect to an earlier measured reference impedance distribution integrated over the electrode plane; and recording a global impedance change curve as a function of time;
  performing breath detection in order to identify a breathing cycle;
  subdividing each breathing cycle to define a plurality of intratidal intervals;
  subdividing an EIT image from each interval into a plurality of regions of interest and calculating for each region of interest the ratio of the integrated impedance change within this region of interest to the global impedance change of this EIT image;
  for each intratidal interval presenting indications of the ratios determined for the regions of interest to provide an intratidal gas distribution representation for each interval.

The automatic analysis of the intratidal gas distributions in the control and analysis unit may include the examination whether the intratidal gas distribution in the lung at any interval of the inspiration or expiration fulfills one of a number of predetermined criteria, for example whether the intratidal gas distribution of one or more regions is below a low threshold value which indicates a collapse of this region. Furthermore the time dependence of the intratidal gas distribution may be analyzed by comparing two or more successive intervals in order to analyze the dynamics of the breathing activity. For this purpose the control and analysis unit may be arranged to analyze the behavior in the regions of interest over several subsequent intervals during inspiration or expiration in order to identify critical conditions which are reflected by certain patterns of the intratidal gas distribution in the ROIs or by certain patterns in their time development. Such situations to be identified by the control and analysis unit may be implemented as predetermined threshold relationships with regard to the intratidal gas distribution values in the ROIs at one point in time or with regard to their time development. Based on the criteria found fulfilled either a corresponding notification indicative of the criterion can be given to the medical personnel according to predetermined rules programmed in the control and analysis unit, or the control and analysis unit may be arranged to directly adjust the ventilator settings of the ventilation system based on the criteria found fulfilled and the predetermined rules how to change ventilator settings in dependence on the criteria found fulfilled.

The general objective of respiratory optimization based on information contained in the intratidal regional gas distribution is to set PEEP, tidal volume, expiration time and respiratory rate in such a way that throughout the whole inspiratory phase there is no substantial redistribution of regional tidal ventilation present, in other words in intratidal gas distribution in the ROIs is fairly constant over the inspiratory and expiratory phase.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
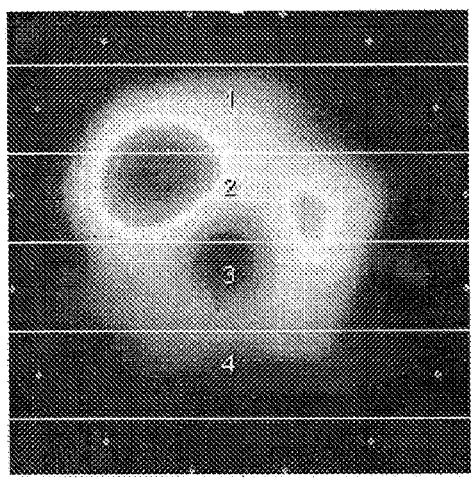
FIG. 1 is an EIT image of a lung in crossed section wherein the grey levels are indicated for the levels of impedance changes.

Referring to the drawings in particular, in FIG. 1 an EIT image of a cross-section of a lung is shown wherein the reconstructed impedance levels are represented by different grey levels. Such EIT image of the cross-section of the lung which is typically taken within the juxtadiaphragmatic plane corresponding to the fifth intercostal space is subdivided into regions of interest (ROI). In FIG. 1 the cross-sectional EIT image of the lung is subdivided into four segments (ROI 1-ROI 4) corresponding to the ventral, midventral, mid-dorsal and dorsal portions of the lung.

Figure 5:
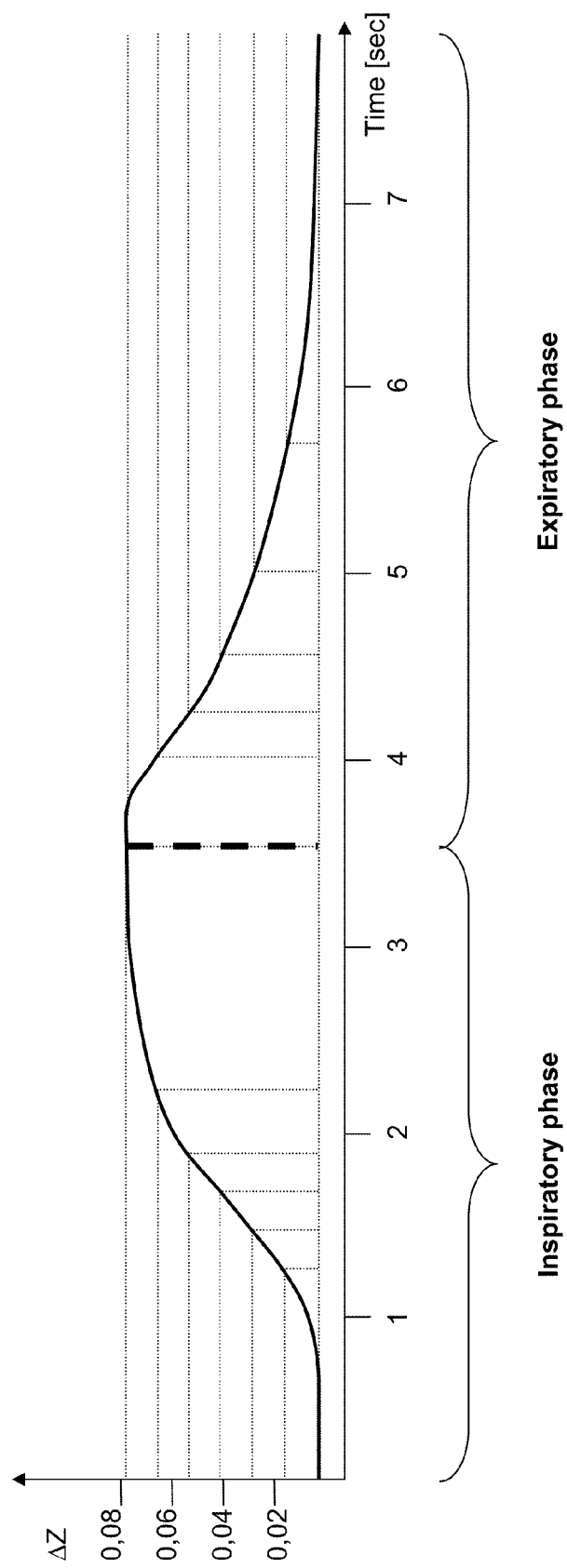
FIG. 5 is a global impedance change curve over one breathing cycle, with equivolume division of both inspiration and expiration into six parts or intervals.
Figure 9:
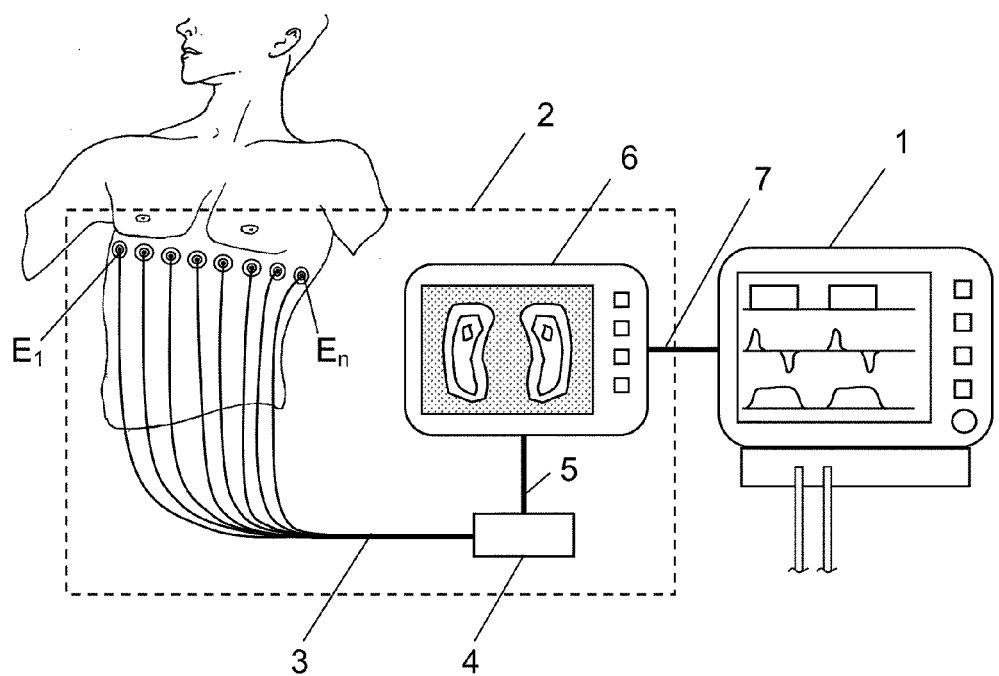
FIG. 9 is a schematic view of an apparatus according to the invention.

FIG. 9 schematically shows an apparatus according to the present invention, optionally connected via data-interface 7 to a ventilator/expirator 1. The EIT imaging device 2 includes a display unit 6 and a control and analysis unit 4 which is connected to the display unit 6 on the one hand and to a plurality of electrodes $E_1, \ldots, E_n$ which are to be placed around the thorax of a patient. The control and analysis unit 4 applies by cables 3 an alternating current to injecting electrodes and senses the voltages measured by the remaining electrodes and successively changes the injection pattern, for example rotating the injecting electrodes around the thorax of the patient in order to collect a number of data sets including the measured voltages corresponding to the various injection patterns. These data sets are reconstructed in the control and analysis unit 4 to provide an EIT-image as shown in FIG. 1 wherein typically the represented image represents the impedance change with respect to an impedance distribution found at a certain reference time, for example the impedance distribution measured before the begin of the inspiration. The EIT images during later intervals of the inspiration and, expiration are then differential images relative to the reference image. The EIT imaging device continuously performs EIT measurements. From these measurements the global impedance curve is derived, wherein the term "global" is used to distinguish this quantity from the measured local or regional impedance distributions. For determining the global impedance change, the impedance change with respect to an earlier reference EIT image is determined and the difference image is integrated to derive the total impedance change as a single parameter. This global impedance change can be displayed as a function of time and corresponds to a volume curve of the breathing cycle. Such global impedance change curve is shown in FIG. 5. The reference EIT image may for example be an EIT image taken before the start of inspiration.

In the global impedance curve algorithms may determine the start and end of inspiration and expiration by functionally analyzing the curve. Thus, the global impedance curve can also be used to determine the breathing cycle. Furthermore, the EIT-images can be analyzed by pattern recognition algorithms in order to determine the boundaries of the lung while the ventilator 1 is performing a vital capacity maneuver, i.e. the inflation of the lungs to a preselected high pressure (typically 40-60 $cmH_2O$) that leads to filling the lung up to its maximal extent. Alternatively, the boundaries of the ventilated part of the lung maybe determined from the end inspiratory status images which represent the ventilated regions of the lung tissue. As the lower boundaries of the lungs might be hard to predict for atelectatic lungs the control and analysis unit may also be provided with stored programs to extrapolate the dorsal boundaries based on the location of the ventral boundaries.

The control and analysis unit is further arranged to subdivide the area in the EIT images within the boundaries determined into two or more regions of interest (ROIs), preferably subdividing the image into segments in ventral-dorsal direction. The ROIs should preferably have the same heights in ventral-dorsal direction so that the gradient of hydrostatic pressure on the lung tissue is the same for each of the ROIs.

In certain clinical conditions it could also be beneficial to subdivide regions for example in the left to right orientation, for example if only one half of the lung is to be examined. Alternatively, the subdivision into regions of interest could be up to the spatial resolution, i.e. each pixel of the image is regarded as a ROI.

The control and analysis unit may further define for example the end expiratory level as the reference level. If the end expiratory levels are varying from breath to breath they can optionally be equalized which means that the end expiratory variation is compensated. Alternatively, the level from the last analyzed image could be taken as a reference.

Furthermore, the control and analysis unit is arranged to divide the inspiratory phase and the expiratory phase into at least two intervals with respect to time or volume (note that global impedance curve is up to a patient individual calibration factor coincident with a volume curve). In FIG. 5 the global impedance curve is for example subdivided according to equal volume or impedance change intervals (see the dotted lines which subdivide the inspiratory phase and the expiratory phase each in 6 intervals with respect to impedance change (=volume)). For each interval the local impedance changes in each region of interest is determined by integrating over this region. To normalize this impedance change in each region of interest it may be divided by the global impedance change at this interval point in time; for each region of interest this ratio is then multiplied by 100 to get a percent value which represents the intratidal gas distribution, or in other words the local contribution of each region of interest to the overall impedance or volume change.

Figure 6:
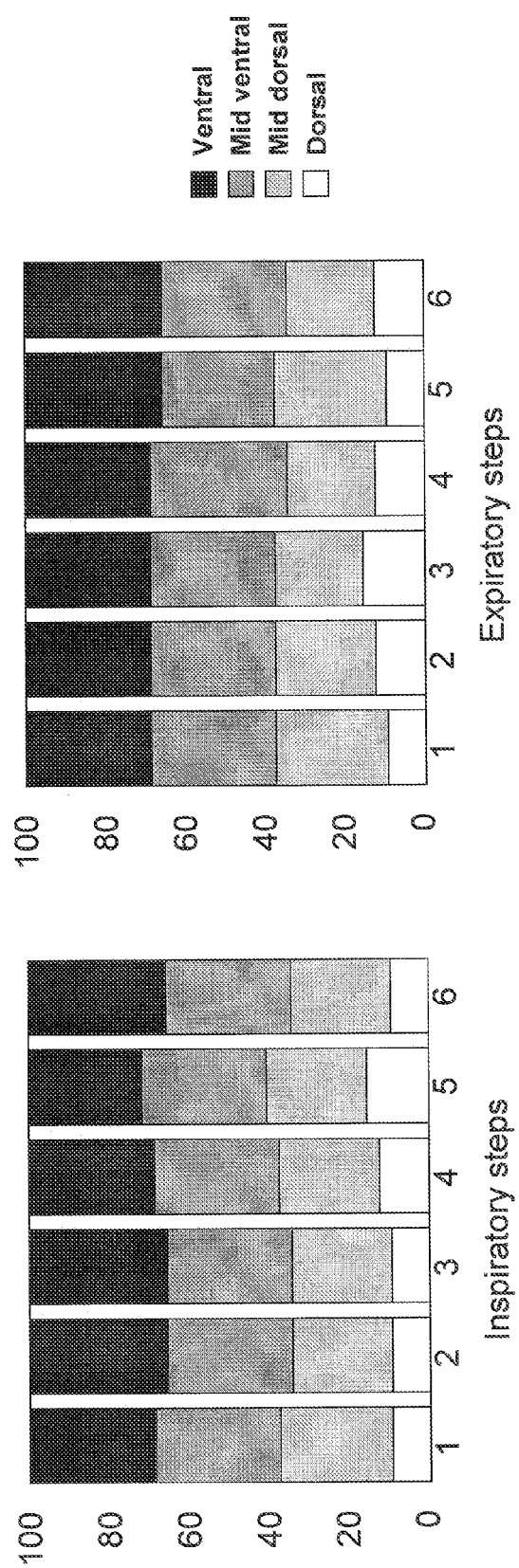
FIG. 6 is a view showing graphical representations of the intratidal gas distribution with 6 intervals during the inspiration phase and 6 intervals during the expiration phase.
Figure 7:
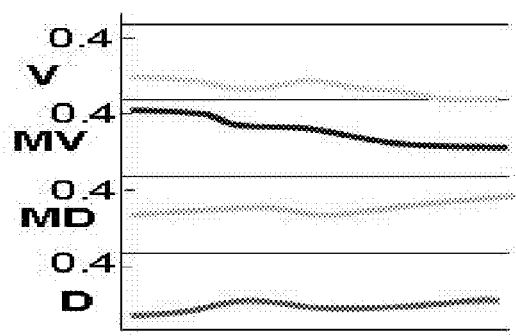
FIG. 7 is an alternative presentation of the intratidal gas distribution in which instead of columns as in FIG. 6 lines connecting the relative contributions of each region of interest to the intratidal volumes are used.

These intratidal gas distribution values may then be presented in a graphical representation, for example on a display. Such display can use bar graphs as for example shown in FIG. 6 where for the six intervals in the inspiratory phase and the six intervals in the expiratory phase the intratidal gas distribution for four ROIs is shown (the regions of interest indicated are ventral, mid-ventral, mid-dorsal, dorsal as indicated in FIG. 1). Alternatively, the intratidal gas distribution values for the inspiratory and expiratory phases may be displayed by a curve over time, each curve representing one region of interest, or as a curve representing the time derivative indicating the change from interval to interval as in FIG. 7 where such lines for ventral (v), mid-ventral (mv), mid-dorsal (rod) and dorsal (d) are shown.

Figure 8:
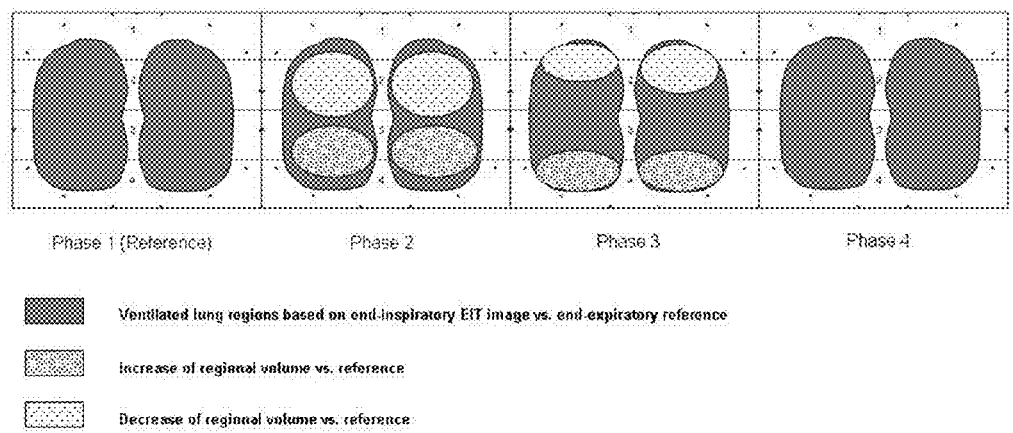
FIG. 8 is an alternative presentation of the time dependence of changes (increase or decrease) of regional impedance (volume) which are indicated compared to a reference (end of expiration)

If intratidal gas distribution is determined pixel by pixel, a series of images can be displayed where the ventilated lung regions are displayed in the background and regions of positive and negative intratidal redistribution are superposed as in FIG. 8. Calculated numerical values and/or indices could also be displayed by the display unit. Another preferred way to display intratidal distribution would be to display e.g. color coded images.

By analyzing the behavior and development in various regions of interest in successive EIT images it is possible to quantify regional changes of end expiratory lung volume (EELV) and of the distribution of tidal volumes (VT). Since a high temporal resolution is possible (typically 20-50 EIT images/second) one may obtain information on the intratidal distribution of gas which describes the changes of regional partial tidal volumes throughout the inspiration or expiration. The intratidal gas distributions thus describe the contribution of each region of interest compared to the sum of all regions of interest at a particular point in time during inspiration or expiration.

In order to better understand the background and the underlying principles of the present invention in the following the results of a clinical study on ALI/ARDS patients obtained with EIT imaging measurements during a so-called recruitment maneuver are described. Recruitment maneuvers are used to reinflate collapsed alveoli wherein e.g. an increased pressure in combination with an increased PEEP is applied over a limited period of time.

Figure 2:
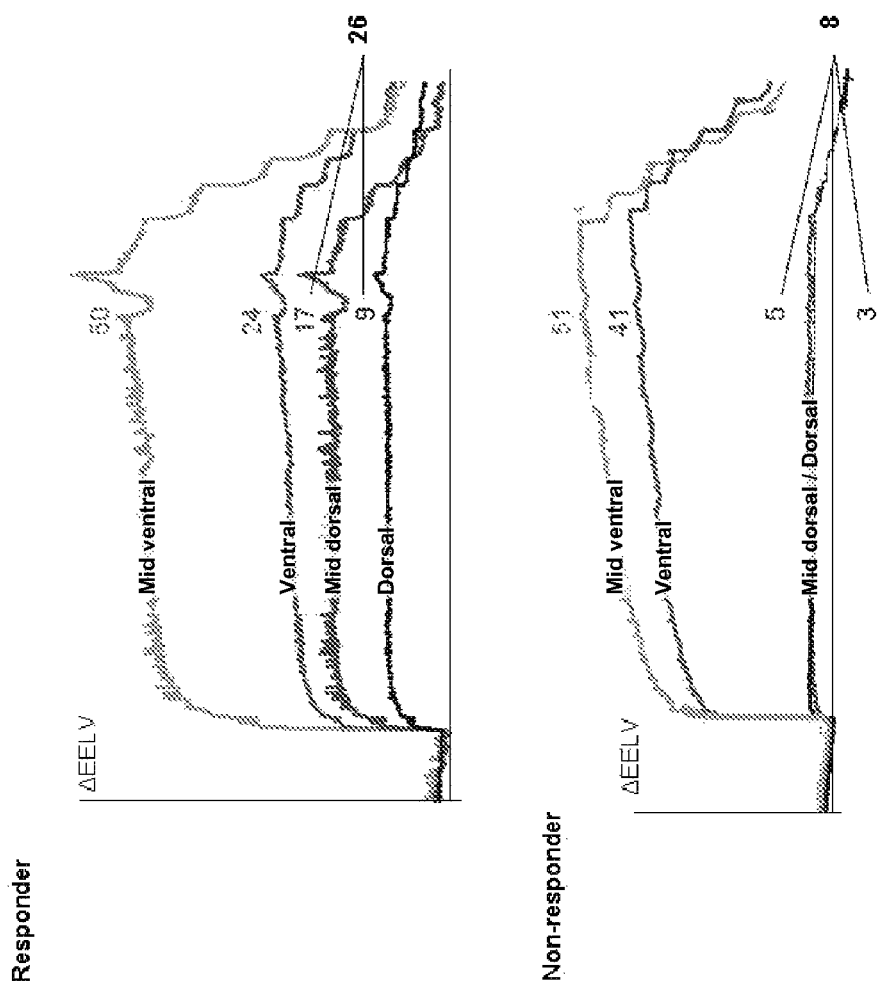
FIG. 2 is a view showing two graphs for the change of the end-expiratory lung volume (EELV) during a recruitment maneuver, in the upper graph for a patient who is responsive to the recruitment maneuver and in the lower part for a patient that does not respond to the recruitment maneuver, wherein in both graphs the respective percent contributions to the change of EELV of four regions of interest are separately indicated (ventral, midventral, mid-dorsal, dorsal)

The results of the study show on the basis of EIT imaging measurements during the recruitment maneuver that there is a completely different behavior with respect to regional EELV and VT during a recruitment maneuver between responders and non-responders, I. e. between patients that are responsive to such maneuver and those who do not show any improvement. FIG. 2 shows graphs of changes in EELV for four regions of interest separately, wherein starting from a baseline a recruitment maneuver with a strong increase in PEEP is performed which causes a corresponding sharp increase in ΔEELV. During the recruitment maneuver the increased PEEP is maintained and thus the ΔEELV remains at the increased level. Thereafter PEEP is stepwise lowered which results in corresponding steps of the ΔEELV in the various regions of interest. In FIG. 2 the upper graph shows the results for a responder and the lower graph for a non-responder to the recruitment maneuver.

For the responder the regional distribution of the increased EELV during the recruitment maneuver was mostly located within two of the regions of interest, namely the ventral and mid-ventral region, but still 26% of the increase occurred in the mid-dorsal and dorsal regions. In contrast for the non-responder hardly any increase is observed in the mid-dorsal and dorsal regions which together only contribute 8% to the increased EELV during the recruitment maneuver.

Figure 3:
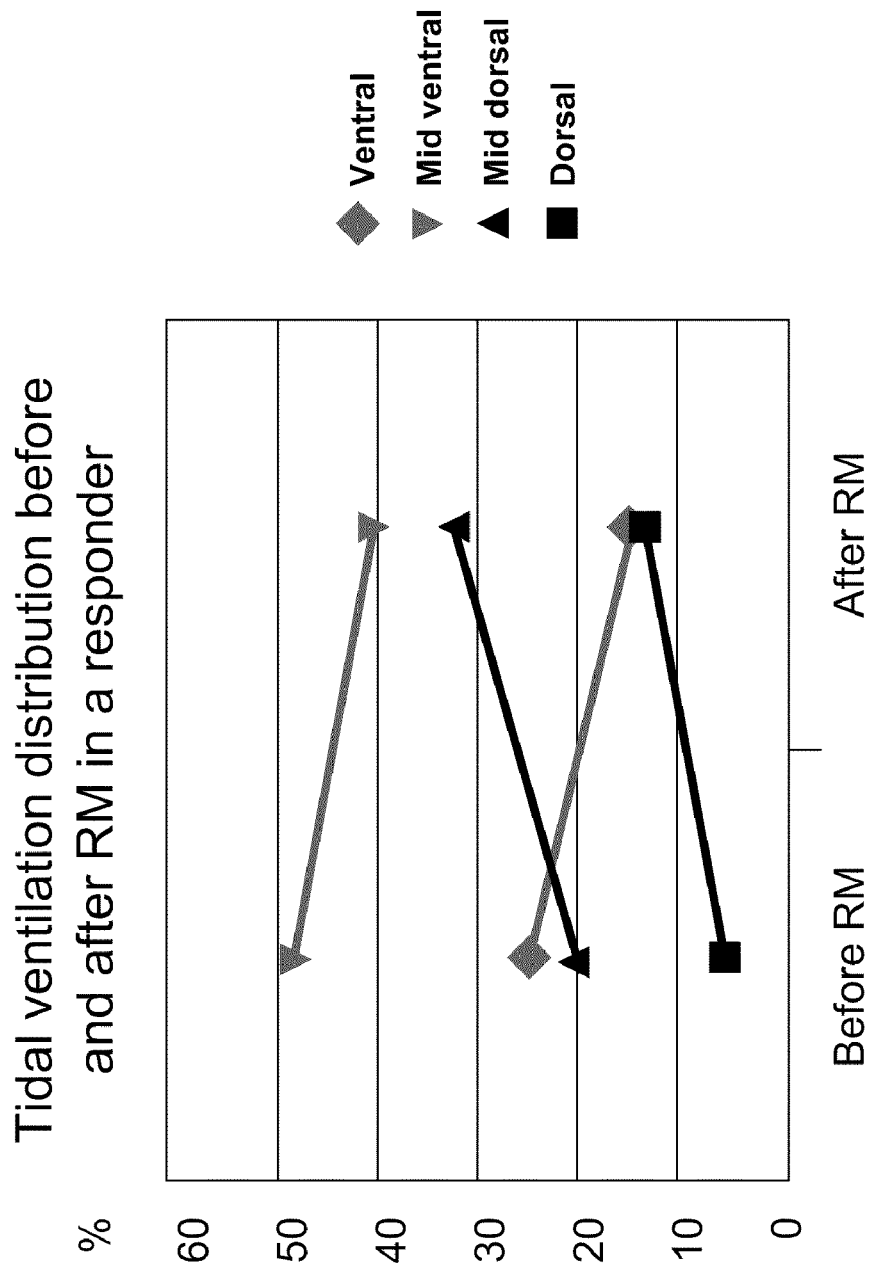
FIG. 3 is a graph showing the regional tidal volume contributions of four regions of interest before a recruitment maneuver and thereafter.

FIG. 3 shows the tidal volume change in percent of tidal volume for four different regions of interest before and after a recruitment maneuver and PEEP increase from 6 to 16 cm $H_2O$, wherein the regions of interest are v=ventral, mv=mid-ventral, md=mid-dorsal and d=dorsal. This graph shows that for a responder the tidal volume distribution shows a considerable development as a result of the recruitment maneuver, with increased percent contributions of the dorsal and mid-dorsal region to the tidal volume. This redistribution was found to be much less pronounced for non-responders.

By analyzing regional alveolar P/V curves using regional volume information obtained by EIT and alveolar pressure from spirodynamic monitoring following explanation for this behavior could be obtained: The dorsal distribution of the tidal ventilation following RM+PEEP increase is caused by the fact the PEEP-increase results in a pronounced increase in ventral EELV as this is the most compliant part of the "wet" ALI/ARDS lung where the superimposed pressure is lowest. This means that when inspiration starts the ventral alveoli of the lung are already in a substantially inflated state and there is very little capacity for additional volume increase before the alveoli are stretched to the structural limit where the regional compliance is approaching zero. This is indicated on the ventral regional alveolar PV-curve as an upper inflection point.

When the compliance of ventral alveoli decreases more and more during the inflation, the compliance of alveoli located more dorsally will exceed the one of the ventral regions at a certain point of time, and as a result gas will move to the more dorsal parts of the lung.

This behavior or mechanism observed during a RM can also be used to describe the conditions during mechanical ventilation on a breath-to-breath level to describe the intratidal redistribution of gas over the regions of the lung area. This redistribution of volume takes place both during the inspiratory and the expiratory phase of ventilation.

These observations have led to the insight that at any point of time always the most compliant part of the lung will receive most volume. Thus, the intratidal distribution of gas is dependent on and will correlate with the regional compliance. A plot of the intratidal gas distribution can be regarded as a compliance versus tidal volume or versus time plot, i.e. it shows what could be regarded as regional lower and upper inflection points (LIP, UIP), but instead of giving the pressure where these LIPs and/or UIPs are situated it provides information where the regional volumes are located during an inspiratory and/or expiratory phase and what the regional compliances are.

Figure 4:
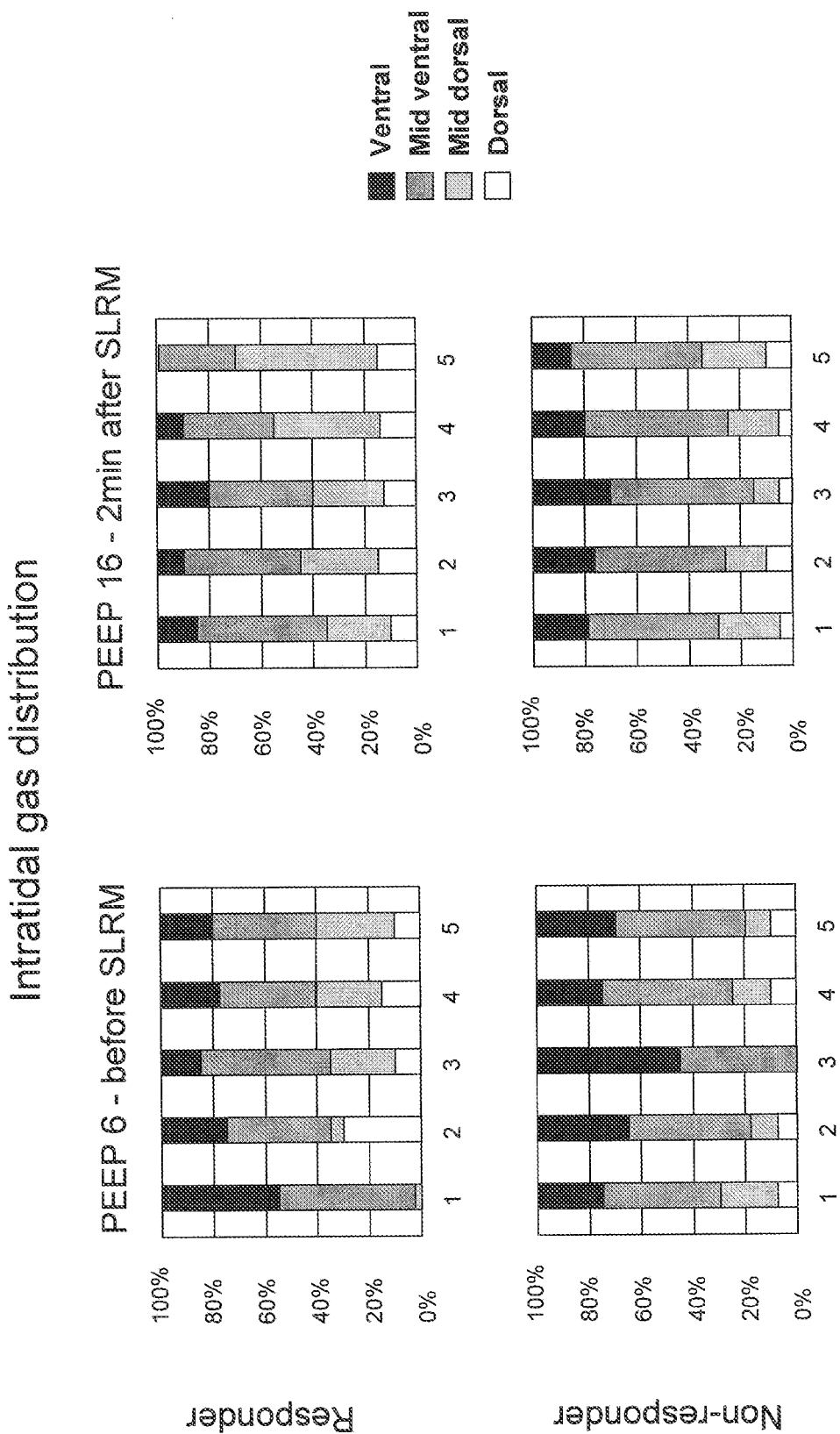
FIG. 4 is a view showing four graphical representations of the intratidal gas distributions, the upper two graphs for a responder to a recruitment maneuver before and after the RM, and the lower two graphs for a non-responder before and after the RM.

FIG. 4 shows the intratidal gas distribution during inspiration obtained according to the present invention before and after a recruitment maneuver, for a responder in the upper two graphs and for a non-responder in the lower two graphs. For a responder it can be seen that initially during inspiration gas goes ventrally and mid-ventrally before the recruitment maneuver. After the RM (upper right graph in FIG. 4) at PEEP of 16 cm $H_2O$ gas enters all regions all the way until the very last part of inspiration when no more gas goes to the most ventral part of the lungs which at that stage are stretched to their structural limit. For the non-responder gas is distributed to all regions fairly evenly throughout the whole inspiration, possibly due to minimal inflammatory edema and lack of recruitable tissue.

When presenting the intratidal gas distribution over time or volume steps of the tidal volume it becomes clear that from this information indications may be derived which according to predetermined rules may be used to give directions to medical personnel to modify the settings of a ventilation system or to automatically modify the settings in order to improve efficiency and to avoid possible dangerous conditions.

The automatic analysis of the intratidal gas distributions in the control and analysis unit 4 may include the examination whether the intratidal gas distribution at one interval of the inspiration or expiration fulfills one of a number of predetermined criteria, for example whether the intratidal gas distribution of one or more regions is below a low threshold value which indicates a collapse of this region. Furthermore the development of the intratidal gas distribution over two or more successive intervals may be examined whether one of a number of further criteria is fulfilled, i.e. for example if the intratidal gas distribution in one region of interest exceeds a threshold value from one interval to the next which indicates a critical condition. Based on the criteria found fulfilled either a corresponding advise can be given to the medical personnel according to predetermined rules programmed in the control and analysis unit 4 based on the criteria found fulfilled, or the control and analysis unit 4 may, through an interface, directly adjust the ventilator based on the criteria found fulfilled and the predetermined rules how to change a ventilator setting in dependence on the criteria found fulfilled. An advice could e.g. be to adjust the PEEP level or to initiate a recruitment maneuver under certain predefined conditions. In the latter case the apparatus may be provided with a data interface 7 between the ventilator 1 and the EIT control and analysis unit 4 which allows to automatically start a recruitment maneuver (optionally only after approval of the clinician), when the EIT control and analysis unit 4 has found criteria fulfilled which are typical or indicative for a RM responder. The control and analysis unit may be arranged to set off an alarm or give a graphical or text indication or message under specific conditions.

The general objective of respiratory optimization based on information contained in the intratidal regional gas distribution is to set PEEP, tidal volume, expiration time and respiratory rate in such a way that throughout the whole inspiratory phase there is no substantial redistribution of regional tidal ventilation present, in other words in intratidal gas distribution in the ROIs is fairly constant over the inspiratory phase.

The following are examples for the analysis criteria for the intratidal gas distributions and possible reactions to be applied based on the criteria found fulfilled:

1. When there is minimal intratidal redistribution and tidal ventilation occurs also in the dorsal and mid-dorsal regions this indicates that the superimposed pressure is little and the lung fairly healthy and there is no need for a RM, high PEEP or a change of ventilator settings.
2. When there is minimal intratidal redistribution and ventilation is mainly distributed over the ventral regions the collapsed dorsal regions are already consolidated and it is unlikely that they can be opened by an RM. This non response to RM can be confirmed, when the RM is performed and the pattern of intratidal distribution has not substantially changed due to the RM. (as shown in FIG. 4, lower left vs. right diagram).
3. If there is continuous recruitment of dorsal and mid dorsal regions during inspiration accompanied by decrease of ventral tidal ventilation, a patient with those conditions would respond to an RM. This response to RM can be confirmed, when the RM is performed and the pattern of intratidal distribution has substantially changed due to the RM (shown in FIG. 4, upper left vs. right diagram).
4. If there is continuous recruitment of dorsal and mid dorsal regions during inspiration accompanied by decrease of ventral tidal ventilation a patient with those conditions would also benefit from an increase of PEEP. (shown in FIG. 4, upper left diagram).
5. If ventral ventilation goes down successively during inspiration a patient with those conditions would benefit from a further increase of PEEP in order to further open up the dorsal regions at the beginning of inspiration. (shown in FIG. 4, upper right diagram).
6. If ventral ventilation decreases or even disappears at the end of the inspiratory phase the tidal volume should be reduced to avoid overstretching of the ventral lung regions (shown in FIG. 4, upper right diagram).
7. During the expiratory phase analysis of the gas distribution could be performed in order to utilize the effects of intrinsic PEEP on keeping all lung regions open during the whole expiration. If ventral ventilation increases successively during expiration accompanied by decrease or absence of end-expiratory dorsal ventilation a patient with those conditions would benefit from a decrease of the expiration time in order to maintain an intrinsic PEEP throughout the expiration, or from an increase of PEEP.

Optionally, the airway pressure can simultaneously be recorded together with the EIT data, so that regional compliance and its intratidal variations can be determined and the regional LIP and UIP could be identified. (Slow inflation can provide static regional PV curves).

As the airway pressure during ongoing ventilation is up to 70% related to the endotracheal tube resistance, which again is a function of the flow, the alveolar pressure difference between the start and end of each inspiratory or expiratory step is unknown (unless some online methods for the calculation of alveolar pressure are used such as Spirodynamics, SLICE method, or multiple linear regression MLR). The alveolar pressure difference is however approximately equal for all ROIs during the same inspiratory or expiratory step and the compliance of one ROI in relation to the others of the same step can be displayed as ratio ROI-volume/Total volume. Having the airway pressure recorded together with the EIT data the following calculations can be made for each time or volume point (step) of the curves:

$$C\text{step-total} = TV\text{ step-total}/\Delta\text{alveolar step-pressure} = \Sigma C\text{step-ROI}1-n$$

$$C\text{step-ROI}v = TV\text{ step-ROI}v/\Delta\text{alveolar step-pressure}$$

$$C\text{step-ROI}mv = TV\text{ step-ROI}mv/\Delta\text{alveolar step-pressure}$$

$$C\text{step-ROI}md = TV\text{ step-ROI}md/\Delta\text{alveolar step-pressure}$$

$$C\text{step-ROI}d = TV\text{ step-ROI}d/\Delta\text{alveolar step-pressure}$$

$$C\text{step-ROI}n/C\text{step-total equals fractional step-ROI compliance}$$

Optionally, the relationship between regional flow and volume can be used to analyze flow distribution.

Optionally, numerical values and/or indices can be calculated from the local percentages of the intratidal gas distributions in the ROIs. E.g. intratidal ratios of ventral-dorsal distribution can be determined for each point of time during the inspiratory and/or expiratory phase. Also, the intratidal standard deviation for each of the regions could be calculated over the inspiratory and/or expiratory phase. If airway pressure is simultaneously recorded, intratidal compliance vs. time diagrams can be displayed instead of impedance vs. time diagrams.

If regional flow distribution has been determined, intratidal flow vs. time diagrams can be displayed instead of impedance vs. time diagrams. Ideally, no region should have a no flow condition during start of inspiration (tidal recruitment, PEEP needs to be increased) nor during end of inspiration (overstretching, tidal volume needs to be decreased).

The control and analysis unit could also be adapted to actively look for the optimal PEEP level for an individual patient: Either, the control and analysis unit 4 could control the ventilator 1 to stepwise increase the PEEP level while analyzing the intratidal gas distribution, and to keep the PEEP level when no substantial intratidal redistribution is observed in the regions of interest. Alternatively, the control and analysis unit 4 could be adapted to start this procedure at a high predefined PEEP level and then to stepwise decrease the PEEP until the control and analysis unit 4 detects a state in the intratidal gas distribution patterns where no substantial intratidal redistribution is present.

Furthermore, the control and analysis unit 4 could be adapted to analyze the expiratory phase and, based on the found pattern and stored adjustment rules, to control ventilator 1 settings: for example, the expiratory time could be titrated by prolonging the inspiratory time until regional expiratory flow is maintained in all regions until the start of the next inspiratory time until regional expiratory flow is maintained in all regions until the start of the next inspiratory cycle.

While specific embodiments of the invention have been described in detail to illustrate the application of the principles of the invention, it will be understood that the invention may be embodied otherwise without departing from such principles.

What is claimed is:

1. An apparatus for determining functional lung characteristics of a patient, the apparatus comprising:
    an electrical impedance tomography (EIT) imaging device with an electrode plane for recording a impedance distribution within a plane of a thorax of the patient, the EIT imaging device including a control and analysis unit for performing an impedance measurement and deriving the impedance distribution within the plane of the thorax (EIT image), the control and analysis unit automatically performing the steps as follows:
    determining a global impedance change, defined as an impedance change with respect to an earlier measured reference impedance distribution integrated over the electrode plane, and recording a global impedance change curve as a function of time;
    performing breath detection in order to identify one or more breathing cycles;
    subdividing each of said one or more breathing cycles to define a plurality of intratidal intervals;
    subdividing an EIT image from each of said intratidal intervals into a plurality of regions of interest and calculating for each region of interest a ratio of an integrated impedance change within one of said regions of interest to the global impedance change of said EIT image; and
    for each intratidal interval presenting indications of the ratio determined for each of the regions of interest to provide an intratidal gas distribution representation for each of said intratidal intervals.

2. An apparatus according to claim 1, wherein the control and analysis unit averages data from at least two breathing cycles in order to obtain the intratidal gas distributions per region of interest.

3. An apparatus according to claim 1, wherein the control and analysis unit analyzes whether patterns of the intratidal gas distribution in the regions of interest fulfill one of a number of predetermined criteria in one interval or development of the patterns of the intratidal gas distribution in the regions of interest over two or more intervals fulfills one of a number of further criteria and to provide a graphical or acoustical notification indicating the criterion is found fulfilled.

4. An apparatus according to claim 1, further comprising:
    an interface of a ventilator of an artificial respiration system wherein the control and analysis unit is connected to the interface.

5. An apparatus according to claim 4, wherein the control and analysis unit is further arranged to analyze the intratidal gas distributions whether patterns of the intratidal gas distribution in the regions of interest fulfill one of a number of predetermined criteria in one interval or development of said patterns over two or more intervals fulfills one of a number of further criteria and to provide in dependence of the criterion found fulfilled and according to stored relationships, control commands for the operation of the ventilator.

6. An apparatus according to claim 1, wherein the control and analysis unit is further arranged to analyze EIT images to identify boundaries of the lung in the EIT images and to subdivide the area within the determined boundaries into regions of interest.

7. An apparatus according to claim 1, wherein said control and analysis unit sets one or more of positive end expiratory pressure, tidal volume, expiration time and respiratory rate based on said intratidal gas distribution representation.

8. A method for determining functional lung characteristics of a patient utilizing an electrical impedance tomography (EIT) imaging device adapted to record an impedance distribution within a plane of the thorax of the patient, the EIT imaging device including a control and analysis unit for performing an impedance measurement and deriving the impedance distribution within the plane of the thorax (EIT image), wherein the following steps are automatically performed:
    determining a global impedance change, defined as the impedance change with respect to an earlier measured reference impedance distribution integrated over the electrode plane, and recording a global impedance change curve as a function of time;
    performing breath detection in order to identify at least one breathing cycle;
    subdividing said at least one breathing cycle to define a plurality of intratidal intervals;
    subdividing an EIT image from each of said intratidal intervals into a plurality of regions of interest and calculating for each region of interest a ratio of an integrated impedance change within one of said regions of interest to the global impedance change of said EIT image; and
    for each intratidal interval presenting the ratio determined for all regions of interest to provide intratidal gas distributions per region of interest for each interval.

9. A method according to claim 8, wherein for each region of interest the data of corresponding intervals from at least two breathing cycles are averaged in order to obtain averaged intratidal gas distributions per region of interest.

10. A method according to claim 9, wherein the intratidal gas distribution in the regions of interest in an interval is examined as to whether the pattern in the regions of interest is fulfilling one of a number of predetermined criteria or whether the development of the patterns over two or more intervals fulfills one of a number of further criteria, and in case one of the criteria or one of the further criteria is found fulfilled, a graphical or acoustical notification indicating the condition found fulfilled is provided.

11. A method according to claim 8, wherein the intratidal gas distribution in the regions of interest in an interval is examined as to whether the pattern in the regions of interest is fulfilling one of a number of predetermined criteria or whether the development of the patterns over two or more intervals fulfills one of a number of further criteria, and in case one of the criteria or one of the further criteria is found fulfilled, a graphical or acoustical notification indicating the condition found fulfilled is provided.

12. A method according to claim 8, wherein initially an EIT image is analyzed to identify boundaries of the lung in the EIT image and regions of interest are defined by subdividing the area within the determined boundaries into regions of interest.

13. An apparatus according to claim 7, wherein said control and analysis unit determines a change in one or more of end expiratory lung volume and tidal volume in each of said regions of interest based on said intratidal gas distribution representation.

14. An apparatus according to claim 13, wherein said regions of interest comprise a ventral portion of a lung, a mid ventral portion of the lung, a mid dorsal portion of the lung, and a dorsal portion of the lung.

15. An apparatus according to claim 14, wherein said control and analysis unit records airway pressure, said control and analysis unit determining a compliance of each said region of interests based on at least said EIT image and said airway pressure.

16. A method according to claim 8, wherein said control and analysis unit sets one or more of positive end expiratory pressure, tidal volume, expiration time and respiratory rate based on said intratidal gas distribution representation.

17. A method according to claim 16, wherein said control and analysis unit determines a change in one or more of end expiratory lung volume and tidal volume in each of said regions of interest based on said intratidal gas distribution representation.

18. A method according to claim 17, wherein said regions of interest comprise a ventral portion of a lung, a mid ventral portion of the lung, a mid dorsal portion of the lung, and a dorsal portion of the lung.

19. A method according to claim 18, wherein said control and analysis unit records airway pressure, said control and analysis unit determining a compliance of each said region of interests based on at least said EIT image and said airway pressure.

20. An apparatus for determining functional lung characteristics of a patient, the apparatus comprising:
   an electrical impedance tomography (EIT) imaging device with an electrode plane for recording a impedance distribution within a plane of a thorax of the patient, the EIT imaging device including a control and analysis unit for performing an impedance measurement and deriving the impedance distribution within the plane of the thorax (EIT image), the control and analysis unit automatically performing the steps as follows:
   determining a global impedance change, defined as an impedance change with respect to an earlier measured reference impedance distribution integrated over the electrode plane, and recording a global impedance change curve as a function of time;
   identifying one or more breathing cycles based on said global impedance change curve;
   subdividing each of said one or more breathing cycles to define a plurality of intratidal intervals;
   subdividing an EIT image from each of said intratidal intervals into a plurality of regions of interest and calculating an intratidal gas distribution ratio for each region of interest, said intratidal gas distribution ratio corresponding to a ratio of an integrated impedance change within one of said regions of interest to the global impedance change of said EIT image;
   providing an intratidal gas distribution representation based on said intratidal gas distribution ratio for each of said intratidal intervals, said intratidal gas distribution corresponding a contribution of each of said regions of interest to said global impedance change; and
   setting one or more of positive end expiratory pressure, tidal volume, expiration time and respiratory rate based on said intratidal gas distribution representation.

* * * * *